United States Patent [19]

Chlanda et al.

[11] Patent Number: 5,198,086
[45] Date of Patent: Mar. 30, 1993

[54] ELECTRODIALYSIS OF SALTS OF WEAK ACIDS AND/OR WEAK BASES

[75] Inventors: Frederick P. Chlanda, Rockaway; Krishnamurthy N. Mani, Basking Ridge, both of N.J.

[73] Assignee: Allied-Signal, Morristown, N.J.

[21] Appl. No.: 632,264

[22] Filed: Dec. 21, 1990

[51] Int. Cl.⁵ ............................................. B01D 61/00
[52] U.S. Cl. .............................. 204/182.4; 204/182.5; 204/301
[58] Field of Search ............... 204/182.4, 182.5, 182.3, 204/301

[56] References Cited

U.S. PATENT DOCUMENTS

| | | | |
|---|---|---|---|
| 2,829,095 | 4/1958 | Oda et al. | 204/98 |
| 3,705,015 | 12/1972 | Chlanda et al. | 204/180 P |
| 4,024,043 | 5/1977 | Dege et al. | 204/296 |
| 4,082,835 | 4/1978 | Chlanda et al. | 423/242 |
| 4,107,015 | 8/1978 | Chlanda et al. | 204/180 P |
| 4,107,264 | 8/1978 | Nagasubramanian et al. | 204/182.4 |
| 4,116,889 | 9/1978 | Chlanda et al. | 521/27 |
| 4,238,305 | 12/1980 | Gancy et al. | 204/180 P |
| 4,391,680 | 7/1983 | Mani et al. | 204/182.4 |
| 4,536,269 | 8/1985 | Chlanda et al. | 204/182.4 |
| 4,552,635 | 11/1985 | Jenczewski et al. | 204/182.4 |
| 4,636,289 | 1/1987 | Mani et al. | 204/182.4 |
| 4,738,764 | 4/1988 | Chlanda et al. | 204/296 |
| 4,740,281 | 4/1988 | Chlanda et al. | 204/151 |
| 4,766,161 | 8/1988 | Chlanda et al. | 521/27 |
| 4,880,513 | 11/1989 | Davis et al. | 204/182.4 |
| 4,976,838 | 12/1990 | Mani et al. | 204/182.3 |
| 5,006,211 | 4/1991 | Paleologou et al. | 204/182.4 |
| 5,034,105 | 7/1991 | Berglund et al. | 204/182.4 |
| 5,049,250 | 9/1991 | Chlanda | 204/182.4 |

FOREIGN PATENT DOCUMENTS 0242784 10/1987 European Pat. Off. .

OTHER PUBLICATIONS

McGraw Chem. Eng. Series "Molecular Diffusion in Fluids" Trebal Mass Transfer Operations 2nd ed. p. 21 1955, 1968.

New Membrane Materials and Processes for Sep. "Water Splitting Efficiency of Bipolar Membranes", K. K. Sirkar & D. R. Lloyd, Eds. Aiche Symposia 261 (1988).

Co-Ion Transport in Bipolar Membranes, Thomas A. Davis—Graver Water Division American Chemical Society 1986 Southwest Regional Meeting, Nov. 20, 1986.

Primary Examiner—John Niebling
Assistant Examiner—Arun S. Phasge
Attorney, Agent, or Firm—Karen A. Harding; Jay P. Friedenson

[57] ABSTRACT

The present invention relates to a method and related apparatus useful to electrodialytically convert the salt of a strong base and a weak acid to base with improved purity; or the salt of a weak base and a strong acid to acid with improved purity.

10 Claims, 6 Drawing Sheets

ELECTRODIALYSIS OF SALTS OF WEAK ACIDS AND/OR WEAK BASES

BACKGROUND OF THE INVENTION

1. Field of the Invention

This invention relates to an improved method for electrodialysis of salts of weak acids and/or weak bases. More particularly; the invention relates to a method used to obtain high purity base from the salt of a weak acid such as sodium formate; or high purity acid from the salt of a weak base, such as ammonium nitrate.

2. Description of Related Art

Electrodialysis uses direct current as a means to cause the movement of ions in solutions. Electrodialysis processes are well known in the art and are typically carried out in a stack arrangement comprising a plurality of flat sheet membranes. The stack consists of electrodes (anode and cathode) at either end and a series of membranes and gaskets which are open in the middle to form a multiplicity of compartments separated by the membranes. Usually, a separate solution is supplied to the compartments containing the electrodes. Special membranes may be placed next to the electrode containing compartments in order to prevent mixing of the process streams with the electrode streams. The majority of the stack between the electrode compartments comprises a repeating series of units of different membranes with solution compartments between adjacent membranes. This repeating unit is called the unit cell, or simply, a cell. Solution is typically supplied to the compartments by internal manifolds formed as part of the gaskets or by a combination of internal and external manifolds. The stacks can include more than one type of unit cell. Streams may be fed from one stack to another in order to optimize process efficiency. Usually the change in composition of a stream after one pass through the stack is relatively small and the solutions can be recycled by being pumped to and from recycle tanks. Addition of fresh solution to and withdrawal of product from the recycle loop can be made either continuously or periodically in order to control the concentration of products in a desired range.

Treatment of aqueous salt streams by electrodialysis to form acid and/or base from the salt is known. The aqueous salt stream is fed to an electrodialytic water splitting apparatus which comprises an electrodialysis stack and a means for electrodialytically splitting water. A useful apparatus is disclosed in U.S. Pat. No. 4,740,281. A useful means to split water to (H+) and (OH−) is a bipolar membrane such as disclosed in U.S. Pat. No. 4,766,161. The bipolar membrane is comprised of anion selective and cation selective layers of ion exchange material. In order for the membrane to function as a water splitter, the layers must be arranged so that the anion layer of each membrane is closer to the anode than the cation layer. A direct current passed through the membrane in this configuration will cause water splitting with hydroxyl ions being produced on the anode side and a corresponding number of hydrogen ions being produced on the cathode side of the membrane. The disassociated salt anions move toward the cathode and the disassociated salt cations move toward the anode.

Electrolytic water-splitting in a two-compartment cell has been disclosed, for example, in U.S. Pat. No. 4,391,680 relating to the generation of strongly acidified sodium chloride and aqueous sodium hydroxide from aqueous sodium chloride. U.S. Pat. No. 4,608,141 discloses a multi-chamber two-compartment electrodialytic water splitter and a method for using the same for basification of aqueous soluble salts. U.S. Pat. No. 4,536,269 disclose a multi-chamber two-compartment electrodialytic water splitter and a method for using the same for acidification of aqueous soluble salts. These two patents review the use of two-compartment electrodialytic water splitters to treat salts.

Three-compartment electrodialytic water splitters are disclosed to be comprised of alternating bipolar, anion and cation exchange membranes thereby forming alternating acid, salt and base compartments. U.S. Pat. No. 4,740,281 discloses the recovery of acids from materials comprising acid and salt using an electrodialysis apparatus to concentrate the acid followed by the use of an electrodialytic three-compartment water splitter to separate the acid from the salt.

The purity of the acids and bases produced from salts by water-splitting is sometimes inadequate. A major source of contamination of the acid and base results from the transport of anions from the acid to the base and cations from the base to the acid. These processes are described in Sirkar et al., Editors, *New Membrane Materials and Processes for Separation;* Chlanda et al., *Water Splitting Efficiency of Bipolar Membranes,* AIChE Symposium Series 1988 and the presentation of T. A. Davis, "Coion Transport in Bipolar Membranes", American Chemical Society, 1986 Southwest Regional Meeting, Nov. 20, 1986. The problem becomes even more severe when weakly ionized acids and bases are being produced. A particular source of contamination is the diffusion of the nondisassociated acid or base across the membranes. These transport processes which result in contamination of the acid and/or base products are illustrated in FIG. 1.

Means to purify acids and bases by the use of bipolar membranes have been described in U.S. application Ser. No. 278,062, filed Dec. 1, 1988, and U.S. Pat. No. 4,976,838. These processes are general to acids and bases obtained from any sources, including the water-splitting operation.

SUMMARY OF THE INVENTION

The present invention relates to a method and related apparatus useful to electrodialytically convert the salt of a strong base and a weak acid to base with improved purity; or the salt of a weak base and a strong acid to acid with improved purity.

For the purpose of the present invention strong bases or acids are those which substantially disassociate in an aqueous solution. Weak acids or bases tend not to disassociate in an aqueous solution. The ionization constant of weak acids or bases is relatively low, typically less than $10^{-3}$ to as low as $10^{-11}$.

A difficulty when electrodialytically treating the salt of a weak/acid base to form weak acid or base is that the weak acid or the weak base of tends to form non-disassociated or non-ionized material in the aqueous solution. Such material having a neutral charge is substantially unaffected by the electrical potential across the electrodialysis cell. The movement of such materials is substantially affected by a concentration gradient. The rate is theoretically proportional to the concentration gradient, generally following Fick's Law (Trebal, Mass Transfer Operations, 2nd Ed., page 21, McGraw-Hill Chemical Engineering Series, 1955, 1968).

Ion exchange membranes are selective because they exclude ions of the same charge as that attached to their matrix. Membranes can contain high concentrations of weakly ionized substances, with water being a common example. Weakly ionized materials can therefore diffuse across ion selective and bipolar membranes. This occurs, for example, when treating a salt such a sodium formate, which is the salt of a strong base, (sodium hydroxide), and weak acid (formic acid). When it is desired to separate sodium formate into sodium hydroxide and formic acid, the sodium can be separated by the electrical potential gradient across the cell and pass across the cation selective membrane into base product cell to form base with hydroxyl ion therein. However, the formate ion remaining behind in the salt feed compartment reacts with hydrogen ion entering the salt feed compartment to form formic acid which remains substantially as formic acid compound rather than disassociated ions of hydrogen and formate. The formic acid therefore has a high concentration in the salt feed compartment and tends to enter and diffuse through the membranes which define the feed compartment into adjacent compartments, including the base product compartment. The formic acid moving into the base compartment (B) reacts with the sodium hydroxide therein to form sodium formate, the very salt which is sought to be split.

The present invention relates to a method to control the electrodialysis process directed to splitting a salt of a strong acid and a weak base, or a strong base and a weak acid. The concentration of weak acid in strong base is substantially zero regardless of the base concentration. The gradient and hence the diffusion rate of a weak acid between compartments according to Fick's Law, is expected to be independent of base concentration. It has unexpectedly been found that the diffusion of the weak acid across the membranes bounding the base product compartment into the base product compartment is related to the concentration of base in that compartment. Similarly, the diffusion of the weak base across the membranes bounding the acid product compartment into the acid product compartment is related to the concentration of acid in that compartment. It is believed that this is due to the pH gradient in the bounding membranes.

In accordance with the method of the present invention the electrodialysis apparatus is operated to produce a strong base of controlled purity from the salt of a weak acid; and alternatively, to produce a strong acid of controlled purity from the salt of a weak base. The unit cells useful in the method of the present invention are repeating units in series between electrodes. Within each unit cell there are different membranes with solution compartments between adjacent membranes. The beginning and end of a unit cell is arbitrarily chosen to facilitate the understanding of the present invention. The repetition of the units substantially characterize the whole membrane/compartment stack between electrode compartments. For the present purpose the unit cells serially start and end in salt feed compartments, including at least a portion of the salt feed compartments at each end as described below and illustrated in the drawings.

In an embodiment where the method is directed to produce base of controlled purity from a salt of a weak acid, the apparatus comprises at least one cell comprising at least one water splitting means to convert water to hydrogen ion and hydroxyl ion. There is a cation selective membrane adjacent to the water splitting means with a base compartment (B) between the cation selective membrane and the water splitting means located to receive hydroxyl ions from the water splitter means. There is a salt feed compartment (S/A) adjacent to the cation membrane opposite the base compartment (B). The cation selective membrane has an outer surface facing away from the base compartment.

In accordance with the method of the present invention the outer surface of the cation membrane is contacted with a solution of the salt of a weak acid. An aqueous stream is fed to the base compartment (B). A sufficient electrical potential is passed across the cell to cause the introduction of hydroxyl ions from the means for splitting water into the base compartment (B). Cations from the salt compartment (S/A) are transported from the salt solution across the cation membrane into the base compartment (B) to form base. The anions remaining in the salt compartment (S/A) form acid with hydrogen ions, formed by the water splitting means, which pass into the salt compartment (S/A). The concentration of base formed in the base compartment (B) and the concentration of acid which diffuses into the base compartment (B) are monitored. The base concentration in the base compartment (B) is controlled to obtain the desired concentration and ratio of base to salt. This embodiment is particularly useful for the salt of a carboxylic acid and the base of a strong base such as an alkali metal, including Group IA metals. Typical salts are selected from the group consisting of alkali metal formates and alkali metal acetates. Of particular interest is the treatment of sodium formate.

Analogously the present invention includes the operation of an electrodialysis apparatus to produce an acid of controlled purity from a salt of a weak base, such as ammonium hydroxide. The apparatus which is particularly useful in this embodiment comprises at least one water splitting means to convert water to hydrogen ion and hydroxyl ion and an anion selective membrane adjacent to the water splitting means. There is an acid compartment (A) between the anion selective membrane and the water splitting means located to receive hydrogen ion from the water splitting means. There is a salt feed compartment (S/B) adjacent to the anion membrane opposite the acid compartment (A). The anion selective membrane has an outer surface facing away from the acid compartment (A).

The method comprises the steps of contacting the outer surface of the anion membrane with a solution of a salt of a weak base. An aqueous stream is fed to the acid compartment (A). A sufficient electrical potential is applied across the cell to cause the introduction of hydrogen ions from the means for splitting water into the acid compartment (A). Anions are transported from the salt solution across the anion membrane into the acid compartment (A) to form acid. The cations remaining in the salt compartment (S/B) form base with hydroxyl ions passing into the salt compartment (A). The concentration of acid formed in the acid compartment (A) and base which diffuses into the acid compartment (A) are monitored. The acid concentration in the acid compartment (A) is controlled to obtain a desired concentration ratio of acid to salt. Typical salts of weak bases include ammonium salts.

BRIEF DESCRIPTION OF THE DRAWINGS

Corresponding elements in different Figures have the same reference characters, plus a multiple of 100, unless indicated otherwise.

In the Figures the following transport convention was used. Major (desired) transport is indicated by a solid arrow; minor (undesired) transport of ions is indicated by dashed arrows; and diffusion of neutral material (not resulting in current) by wavy arrows.

DESCRIPTION OF THE PREFERRED EMBODIMENT

The preferred embodiments of the present invention will be understood by those skilled in the art by reference to the accompanying Figures.

Figure 1:
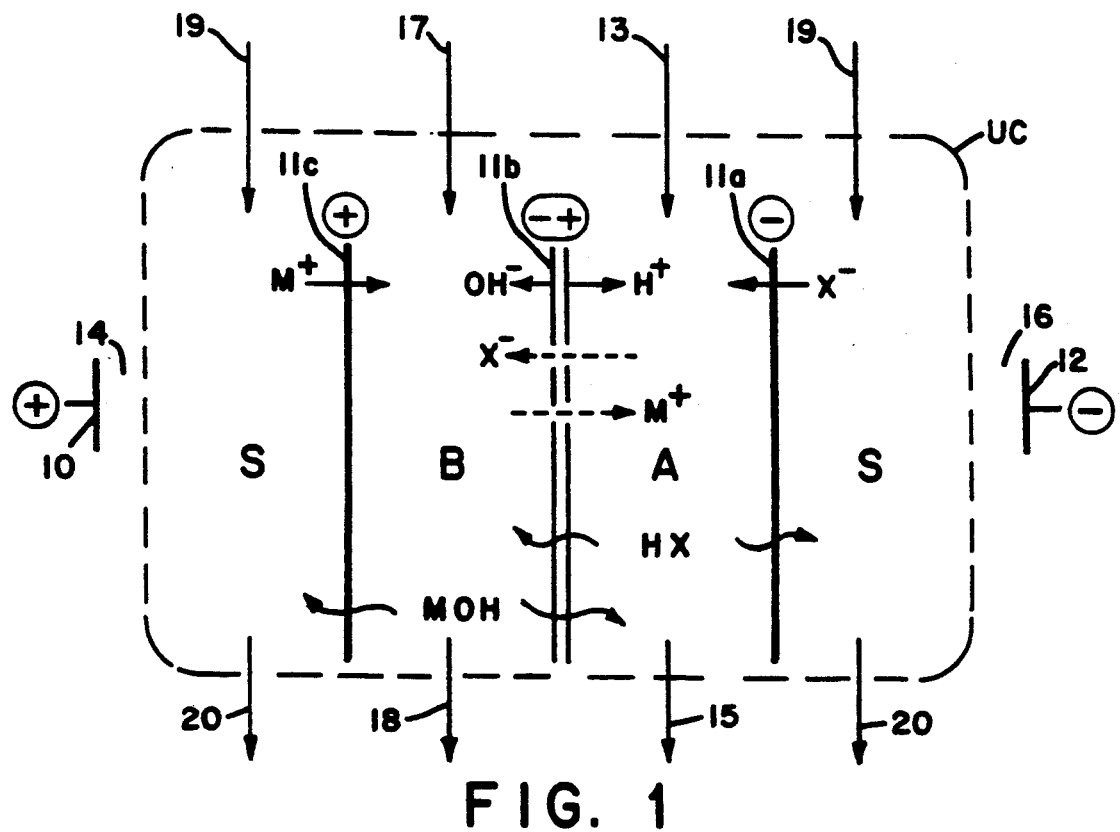
FIG. 1 is a schematic drawing of a three compartment unit cell to illustrate transport phenomena, and which was used in Comparative Example 1.

FIG. 1 is a three-compartment unit cell illustrating ion leakage. The three-compartment electrodialytic water splitter shown in FIG. 1 is used to recover and regenerate acid and base from salt solutions. The water splitter comprises, in series, an anode 10 (e.g., a platinum anode); an anolyte compartment 14; repeating in series of salt (S); base (B); and acid (A) compartments; a catholyte compartment 16; and a cathode 12 (e.g., a platinum cathode). The acid, base and salt compartments (A) of the three-compartment water splitter illustrated in FIG. 1 are defined by a plurality of serially arranged membranes as follows: an anion permselective membrane 11a, a bipolar membrane 11b, and a cation permselective membrane 11c. Although FIG. 1 shows four serially arranged compartments, the three-compartment electrodialytic water splitters are defined by a plurality of unit cells, each unit cell (UC) comprising a cation membrane, a bipolar membrane (or equivalent structure capable of splitting water into hydrogen and hydroxyl ions), and an anion membrane, and related compartments.

The anolyte and catholyte compartments typically contain a base, salt, or acid solution, the acid (A) and base (B) compartments initially contain a liquid comprising water, added via lines 13 and 17, respectively. salt (S) compartment initially contains a salt solution, comprising a salt MX of a cation ($M^+$) and an anion ($X^-$), added via line 19. The designation ($X^-$) refers not only to monovalent anions but also to divalent anions, such as sulfates, and trivalent anions, such as phosphates, and mixtures thereof. Splitting of the salt into acid and base commences by applying an electrical potential between the electrodes causing a direct current.

In the acid compartment (A) which is supplied with a liquid comprising water and preferably an acid, hydrogen ions ($H^+$) are added via the function of the bipolar membrane 11b. Simultaneously, anions ($X^-$) of the salt are transported across the anion membrane 11a into the acid compartment (A). The combination of the hydrogen ions with the anions yields an acid product (HX).

Cations ($M^+$) pass from salt compartment (S) through the cation membrane 11c to the base compartment (B). In the base compartment (B), cations ($M^+$) migrating through the cation membrane 11c combine with the hydroxyl ions ($OH^-$) generated by the bipolar membrane 11b to produce a basified (MOH) solution.

The acid product from compartment (A) is removed via line 15, the base product from the base compartment (B) is removed via line 18, and the depleted salt solution from salt compartment (S) is removed via line 20. The electrodialytic water splitter can be operated in a batch mode, a continuous mode, or variations thereof. Product solutions or portions thereof may be recycled for further concentration.

A source of impurities in the product acid and base is the transport of anions ($X^-$) and acid (HX) across the bipolar membrane to the base compartment (B); and the transport of cations ($M^+$) and base (MOH) across the bipolar membrane to the acid compartment (A). This results in contamination of both the acid and base products with salt.

The amount of contamination depends on the properties of the bipolar membrane, the products being produced, and the operating conditions of the water splitter. Temperature and especially current density may be adjusted to obtain higher purity acid and base. The contamination levels generally are lower when lower temperatures and higher current density are used. The flux of contaminating species also depends strongly on the concentration of the contaminating species in the adjacent compartment. Control of the product concentrations by adding a diluent or in the case of volatile acids and bases by stripping is another means of controlling the level of contamination.

The diffusion of weak electrolytes (e.g., $NH_4OH$, $H_2SO_3$, $H_2S$, formic acid and acetic acid) across the bipolar membrane into the corresponding strong acid or base product compartment is particularly significant when high concentrations of the weak electrolyte are in contact with the bipolar membrane. Typically, weak electrolytes have an ionization constant of $10^{-3}$ or less. When the concentration in the compartment in which they form is low, the diffusion of such weak electrolytes is correspondingly less. Additionally, in accordance with the present invention, it has been found that the concentration of the strong acid or base in their respective product compartments can be monitored and used to control the diffusion of weak electrolytes into these compartments.

Figure 2:
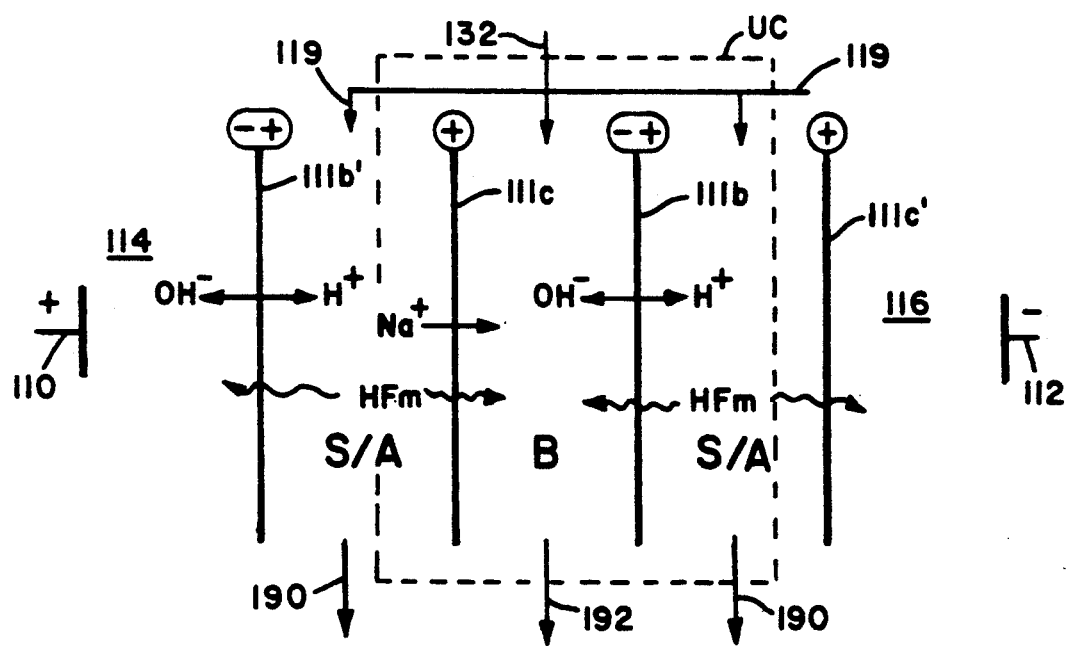
FIG. 2 is a schematic drawing of a two compartment unit cell of the present invention useful for generating base with improved purity.

The present invention includes the treatment of the salt of a strong base and a weak acid such as an alkali formate salt, preferably sodium formate, to obtain formic acid and sodium hydroxide with improved purity. FIG. 2 is a schematic drawing of a 2 compartment water splitter useful to obtain formic acid and sodium hydroxide from sodium formate. The apparatus comprises a plurality of two compartment unit cells (UC). The unit cell comprises a bipolar membrane 111b. The bipolar membranes shown, 111b and 111b', have a cation selective surface (+), and an anion selective surface (−). In the unit cell illustrated in FIG. 2, there is a cation selective membrane 111c adjacent to the anion selective surface (−) of bipolar membrane 111b. There is a base product compartment (B) between the anion selective surface (−) of the bipolar membrane and the cation selective membrane 111c. There are salt/acid compartments (S/A) between the cation selective surface (+) of the bipolar membrane 111b and 111b' and the adjacent cation selective membrane 111c' and 111c respectively.

A salt feed stream 119 such as a stream comprising sodium formate is fed into the salt/acid (S/A) compartments. An aqueous fluid is added via line 132 to the base compartment (B). When an electric field is applied across the cell, via the anode 110 and the cathode 112, water is split at the bipolar membranes resulting in H+ entering into the salt/acid compartment (S/A) and OH− entering into the base compartment (B). Sodium ions migrate through the cation selective membrane 111c into the base compartment (B). The sodium ions combine with the hydroxyl ions to form sodium hydroxide. The formate ions remain in the salt/acid compartment (S/A) and combine with the hydrogen ions to form formic acid. Sodium hydroxide containing product stream 192 is removed from the base compartment (B) and formic acid contained in stream 190 is removed from the salt/acid compartment (S/A). With the salts of weak acids, such as sodium formate, the salt remaining in acid product stream 190 can be reduced to low levels if desired. Some formic acid migrates across both the cation membranes and the bipolar membranes into the base compartments (B) resulting in sodium formate in the base product stream 192.

Weak electrolyte diffusion across the bipolar membrane is particularly significant at high acid concentrations. The formic acid diffusion can be minimized by controlled operation of the electrodialytic water splitter of FIG. 2. The formic acid diffusion can be minimized by running a batch operation on the acid side, (S/A) compartment. The formic acid concentration typically can be raised from essentially nil at the start of the batch, to a final value (e.g., 20%) at the end of the batch. In this way, the average concentration overtime is about one-half of the final value (i.e., 10%).

An alternate but inferior (from the standpoint of base product purity) method would be continuously adding sodium formate to the salt/acid compartment (S/A) and withdrawing product at such a rate that the product contained a desired amount (i.e., 20%) of formic acid. In this type of operation, the average formic acid concentration would be the desired amount (i e., 20%), and consequently more (approximately double) formic acid would be transported to the base across the bipolar membrane.

Figure 4:
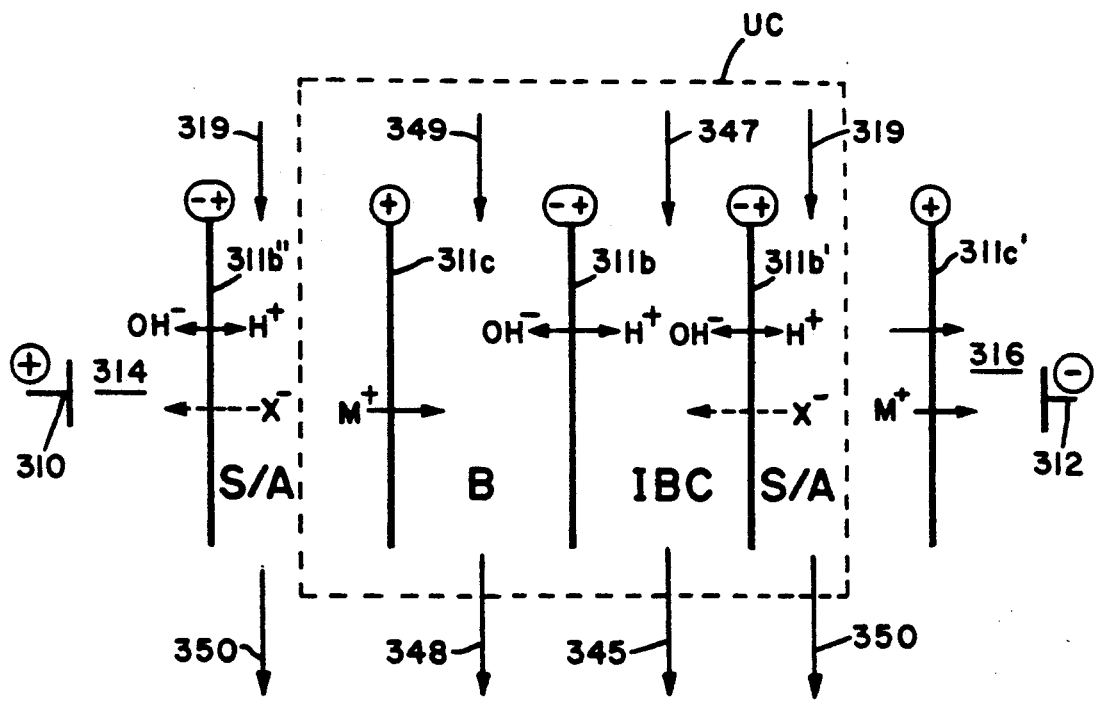
FIG. 4 is a schematic drawing of a unit cell of the present invention useful for generating base with improved purity.

Either of the above processes can be combined with an electrodialytic cell such as shown in FIG. 4, in order to obtain NaOH with improved impurity. In the case of the batch operation, the batch could be run to a desired value (i.e., 10%) of formic acid in the conventional two compartment apparatus (FIG. 2) resulting approximately in an average formic acid concentration of one-half of the final value (i.e., 5%) and a corresponding amount of base contamination. The remainder of the process could then be carried out using the apparatus of FIG. 4 to raise the concentration (i.e., from 10 to 20%). Any formate transported from the salt/acid compartment (S/A), across bipolar membrane 311b' is removed from the intermediate base (IBC) before the formate can migrate across bipolar membrane 311b. In this way formate is substantially prevented from contaminating the base product in base compartment (B), and a base of increased purity and concentration can be obtained.

In the case of the continuous process, the operation of a first stage in a conventional two compartment stack to desired formic acid value (i.e., 10% formic acid) followed by continuous operation to give 20% formic acid in a stack as shown in FIG. 4 will give base of a purity close to that from a batch process (i.e., producing 20% formic acid), but one with the advantage of a continuous process. Many other combinations of continuous and batch operations utilizing water splitters of the conventional type and of the type using at least two adjacent bipolar membranes used for production of higher purity acids and bases are possible.

In addition to the known means to improve purity, it has been found that control of diffusion across the monopolar cation membrane 111c is important to attain high purity base product when splitting alkali metal salts of weak acids, such as sodium formate. Contrary to what is expected, the purity of the base product (NaOH) is improved when the concentration of base in base compartment (B) is high. This apparently results from a reduction in diffusion of formic acid across the cation membrane 111c. A possible explanation is that the pH in the membrane increases as the base concentration increases and the effect of the electric potential gradient on the formate ion produced retards its migration toward the cathode. To produce base of the best purity in sodium formate splitting, it is desirable to operate at concentrations of NaOH of >10 weight percent, preferably >15 weight percent even though such operation might lower the overall process efficiency.

Figure 3:
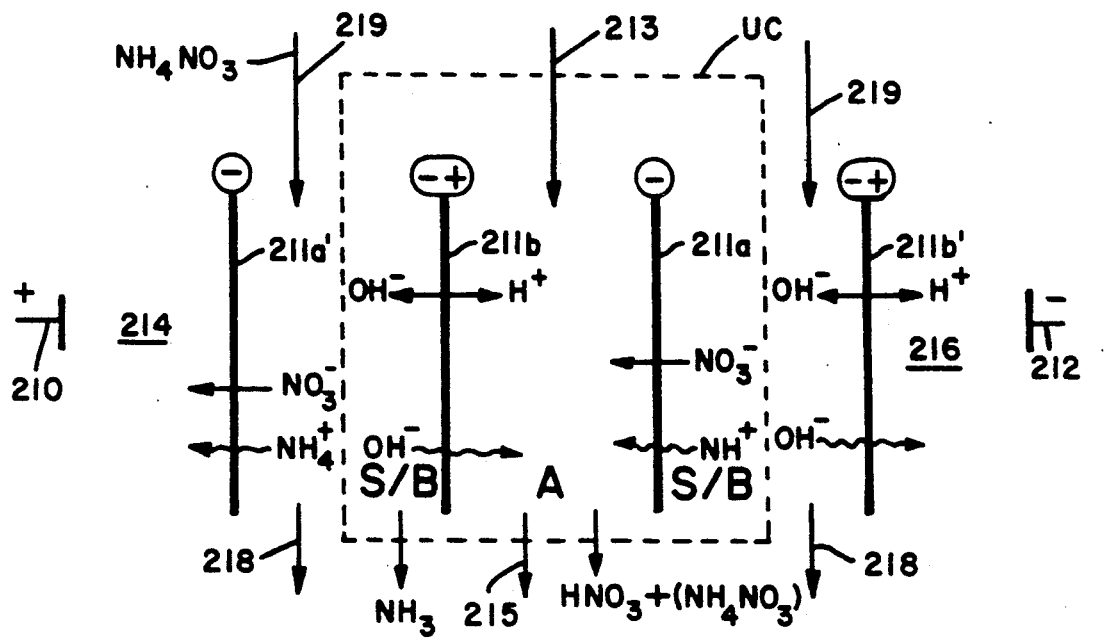
FIG. 3 is a schematic drawing of a two compartment unit cell of the present invention useful for generating acid with improved purity.

The present invention analogously includes the treatment of a salt of a weak base and a strong acid, including ammonium salts, such as ammonium nitrate, to obtain ammonia and nitric acid with improved purity. FIG. 3 is a schematic drawing of a conventional water splitter useful to obtain ammonia and nitric acid from ammonium nitrate. The apparatus comprises a plurality of unit cells (UC). The unit cell comprises a bipolar membrane 211b. The bipolar membranes shown, 211b and 211b', have a cation selective surface (+), and an anion selective surface (−). There is an anion selective membrane 211a adjacent to the cation selective surface (+) of bipolar membrane 211b. There is an acid product compartment (A) between the cation selective surface (+) of bipolar membrane 211b and the anion selective membrane 211a. There are salt/base compartments (S/B) between the anion selective surfaces (−) of the bipolar membranes 211b and 211b' and the adjacent anion selective membranes 211a' and 211a respectively.

A salt feed stream 219 comprising the salt of a weak base and a strong acid, such as ammonium nitrate, is fed into the salt/base (S/B) compartments. An aqueous fluid is added via line 213 to the acid compartment (A). When an electric field is applied across the cell, via anode 210 and cathode 212, water is split at the bipolar membranes resulting in (H+) entering into the acid compartment (A) and (OH⁻) entering into the salt/base (S/B) compartment. Nitrate ions migrate through the anion selective membrane 211a into the acid compartment (A). The nitrate ions combine with the hydrogen ions to form nitric acid. The ammonium ions remain in the salt/base (S/B) compartments and combine with the hydroxyl ions to form ammonium hydroxide. The nitric acid containing product stream 215 is removed from the acid compartment (A) and ammonium hydroxide contained in the product stream from the base 218 is removed from the salt/base (S/B) compartment.

The diffusion of weak electrolytes across the bipolar membranes is particularly significant at high concentrations. The ammonium hydroxide diffusion can be minimized by controlled operation of the electrodialytic water splitter of FIG. 3 in an analogous fashion to the control of formic acid diffusion in the electrodialytic water splitter of FIG. 2. One way is to control the ammonium hydroxide concentration in the salt/acid feed compartment. This can be done in a batch mode. The process is conducted so that the ammonium hydroxide concentration will raise from essentially nil at the start of the batch to a final value corresponding to 10 weight percent ammonium or more at the end of the batch. In this way the average concentration over time is about one-half of the final value.

An alternate way is to continuously add ammonium nitrate to the salt/base (S/B) compartment and withdraw product at such a rate that the product contains a desired amount of ammonium hydroxide. As with the embodiment illustrated in FIG. 2, the embodiment illustrated in FIG. 3 can be used in combination with an electrodialytic cell such as shown in FIG. 4, with cation membranes replaced by anion membranes, in order to obtain acid with improved purity. In addition, because ammonia is a volatile base, its concentration in the base compartment (B) can be minimized by stripping with a vacuum, heat, air or a combination thereof.

In addition to these conventional methods of reducing weak base diffusion and improving acid product purity, when splitting a salt of a strong acid and a weak base, such as ammonium nitrate, it is important to control diffusion across the monopolar anion membrane. In the apparatus of FIG. 3, the purity of the acid product is improved when the concentration in the acid compartment (A) of the acid is high. This apparently results from a reduction in diffusion of ammonium hydroxide across the anion membrane 211a. A possible explanation is that the pH in the membrane decreases as the acid concentration increases and the effect of the electrical potential gradient on the ammonium ion retards its migration toward the anode. To produce acid of the best purity in ammonium nitrate splitting, it is desirable to operate at concentrations of nitric acid of greater than 6 weight percent, preferably greater than 9 weight percent, even though such operation might lower the overall process efficiency.

If greater purity is required than can be achieved in the conventional two compartment cell, even when practicing the method of this invention for controlling the strong acid or base product concentration, a portion of the process can be carried out in an electrodialytic water splitter having a unit cell which comprises at least two adjacent water splitting means, preferably bipolar membranes in series, with an intermediate compartment between adjacent bipolar membranes. The intermediate compartment provides a means of controlling the concentration of the potentially contaminating species next to the acid (A) and base (B) compartments. Because the compartment is between bipolar membranes, most of the ion transport into the compartment consists of entry of hydrogen and hydroxyl ions. These react to form water. Therefore, the ionic composition of the solution changes relatively slowly and it is not necessary to replenish it at a high rate to maintain its composition in a desirable range. The solution introduced to the intermediate compartment can contain an electrolyte of a type and at a concentration such that there is less transport (leakage) of cations (M⁺) across the bipolar membranes bounding the acid compartments if pure acid is being produced; and/or less transport (leakage) of anions (X⁻) across bipolar membranes bounding the base compartments (B) if pure base is being produced. The average composition of solutions within the cell is determined primarily by the influent composition and flow rate, the current density, residence time in the cell and the transport properties of the membranes. It can be estimated readily by one skilled in the art or determined by routine experimentation. Thus, process control can be obtained by control of influent composition and flow rates.

When pure base (a base containing a low level of anions other than hydroxide) is being produced, the electrolyte in the intermediate compartment is preferably a base; and when pure acid (an acid containing a low level of cations other than hydrogen ion) is being produced, the electrolyte in the intermediate compartment is preferably an acid. While the use of acid and base in the intermediate compartments is preferred, salts, especially at low concentration, can be used. The concentration of the electrolyte used in the intermediate compartment affects the product purity. The use of a relatively low concentration can be advantageous in producing simultaneously base and acid of improved purity with only a single intermediate compartment.

The concentration of acid or base in the intermediate compartment is preferably lower than that in the acid or base product compartments, respectively. Typically, the concentration of acid, base, or salt in the intermediate compartment is less than 5 weight percent, and preferably from 1 to 3 weight percent.

A method for generating acid having improved purity from an aqueous solution of the salt of a weak base, comprises the steps of feeding the aqueous salt solution to an electrodialytic apparatus comprising at least two adjacent means for splitting water, there being an intermediate acid compartment (IAC) between adjacent means. At least one anion selective membrane is adjacent to the means for splitting water nearest the cathode. An acid product compartment is between the anion selective membrane and the means for splitting water, and a salt feed compartment is adjacent to the anion selective means on the side opposite the acid product compartment. The aqueous salt solutions are fed to the salt feed compartments. An aqueous stream preferably comprising an acid is fed to the intermediate acid compartment (IAC). An aqueous stream is fed to the acid product compartment. A sufficient electrical potential is applied across the cells to a cause introduction of H⁺ from the means for splitting water into the acid product compartment, and transport of anions from the salt feed compartment into the acid product compartment to form acid in the product compartment. The acid is removed from the product compartment; and the intermediate acid product is removed from the intermediate compartment. Cations and weak base migrating from the base compartment (B) adjacent to the bipolar membrane closest to the anode toward the cathode are collected in the intermediate acid compartment (IAC) for removal.

A method for generating base having improved purity from an aqueous solution of the salt of a weak acid, comprises the steps of feeding the aqueous salt solution to an electrodialytic apparatus comprising at least two adjacent means for splitting water, there being an intermediate base compartment (B) between adjacent means. At least one cation selective membrane is adjacent to the means for splitting water nearest the anode, there being a base product compartment between said cation selective means and the means for splitting water, and a salt feed compartment adjacent to the cation selective means opposite the base product compartment. The aqueous salt solutions are fed to the salt feed compartments. An aqueous stream preferably comprising a base is fed to the intermediate base compartment (B). An aqueous stream is fed to the product base compartment (B). A sufficient electrical potential is applied across the cells to a cause introduction of $OH^-$ from the means for splitting water into the product base compartment (B), and transport of cations from the salt feed compartment into the product base compartment (B) to form base in the product compartment. The base is removed from the base product compartment; and the intermediate base product is removed from the intermediate compartment. Anions migrating from the compartment adjacent to the means for splitting water closest to the cathode toward the anode are collected in the intermediate base compartment (B) for removal.

FIG. 4 illustrates a unit cell (UC) for an apparatus useful to generate base having improved purity by electrodialytically treating an aqueous salt solution. The apparatus comprises an anode 310 and cathode 312. There is an anolyte compartment 314 between the anode and at least one and preferably at least two unit cells. There is a catholyte compartment 316 between the cathode 312 and the at least two unit cells.

Each unit cell comprises at least two means for splitting water, preferably bipolar membranes 311b and 311b', which are in series and adjacent to each other. Each bipolar membrane has a cation layer (+) and an anion layer (−). The cation layers face the cathode 312 and the anion layers face the anode 310. The bipolar membranes are adjacent to each other, there being an intermediate base compartment (IBC) between them. Adjacent to the cation layer (+) of the bipolar membrane 311b' nearest the cathode there is a cation membrane 311c' which can be part of an adjacent unit cell. Salt feed compartment (salt/acid compartment S/A) is between cation membrane 311c' and bipolar membrane 311b. There is another cation membrane 311c adjacent to the anion layer (−) of bipolar membrane 311b on the side opposite from 311b'. Base product compartment (B) separates cation membrane 311c and bipolar membrane 311b. Adjacent to cation membrane 311c on the side opposite of base compartment (B) is a salt/acid compartment (S/A). The salt/acid compartment is defined by the cation membrane 311c and bipolar membrane 311b'' of an adjacent unit cell.

A salt feed stream 319 is fed into the salt/acid base (S/A) compartments. An aqueous fluid is added via line 349 to base product compartment (B). An aqueous stream preferably comprising a base is fed via stream 347 into intermediate base compartment (IBC). When the electric field is applied across the cell via the anode 310 and cathode 312, water is split at bipolar membranes resulting in $OH^-$ entering the intermediate base compartment (IBC) and the base compartment (B). Hydrogen ions ($H^+$) formed by the bipolar membranes enter the intermediate base compartment (IBC) and the salt/acid compartment (S/A). Cations ($M^+$) migrate across the cation membranes towards the cathode 312. Because bipolar membrane 311b' is not perfectly selective, some anions ($X^-$) migrate from the salt/acid (S/A) compartment toward the base product compartment (B). Additionally, anion transport results from diffusion of weak acid across the cation layer of the bipolar membrane to the interface where it is split to ($X^-$) and ($H^+$). The anions ($X^-$) leaking across the bipolar membrane 311b' enter the intermediate base compartment (IBC). The concentration of anions ($X^-$) in compartment (IBC) can be controlled by the concentration (i.e., presence of base), and/or the rate of make-up in stream 347 and withdrawal in stream 345. The feed rate and composition of stream 347 can be used to assure that there is no precipitation in the (IBC), and that the flux of anions across the membrane 311b to the base compartment (B) is minimized. Acidified salt is removed via line 350 and pure base is removed via line 348.

Useful bipolar membranes comprise a cation layer (+) and an anion layer (−). The cation layer permits the cations to pass through and the anion layer permits anions to pass through. The cation layer is a barrier to anions and the anion layer is a barrier to cations. Useful cation membranes permit cations to pass through and are a barrier to anions, and similarly useful anion membranes permit anions to pass through and are a barrier to anions.

Examples of bipolar membranes which are particularly useful include those described in U.S. Pat. No. 2,829,095 to Oda, et al. (which has reference to water splitting generally), in U.S. Pat. No. 4,024,043 (which describes a single film bipolar membrane), and in U.S. Pat. No. 4,116,889 (which describes a cast bipolar membrane and is most preferred) and U.S. Pat. No. 4,082,835. However, any means capable of splitting water into hydrogen and hydroxyl ions may be used; for example, spaced apart anion and cation membranes having water disposed therebetween.

Useful cation membranes employed can be moderately acidic (e.g., phosphonic group-containing) or strongly acidic (e.g., sulfonic group containing) cation permselective membranes having a low resistance at the pH at which they are employed. Particularly useful cation membranes are DuPont's Nafion ® 110 and 324 cation membranes and Asahi Glass CMV cation membranes. More preferably, the cation membranes are of the composition and construction as disclosed in U.S. Pat. No. 4,738,764, to Chlanda, et al. and commonly assigned.

Useful anion membranes include strongly, mildly, or weakly basic anion membranes. Commercially available anion membranes include those from Ionics, Inc., Watertown, Mass. (sold as Ionics 204-UZL-386 anion membrane), or from Asahi Glass Co. (sold under the trade name Selemion ® AMV AAV, ASV anion permselective membranes).

In accordance with the apparatus and method of the present invention a wide variety of soluble salts can be electrodialyticly treated to form acids and bases. The salts which are treated in accordance with the process of the present invention are the salts of weak acids and/or bases. The salt cations include mono, di and trivalent metallic and non-metallic cation including ammonium. The anions include monovalent anions such as halides and carboxylates, divalent anions, such as sulfates and dicarboxylates, trivalent anions, such as phosphates and mixtures thereof. Typical salts which can be treated include sodium formate, sodium acetate, sodium lactate, sodium citrate, $NH_4Cl$, $NH_4NO_3$, $(NH_4)_2SO_4$, and trimethylammonium chloride. Mixtures of salts can also be treated.

The salt feed can be at concentrations up to saturation, preferably, from 0.1 molar to saturation concentration, and are typically 0.5 molar or more. Preferably, the concentration of the purified acid or base in the product stream is 0.5N to 5N and most preferably, 1 to 3N.

Useful operating temperatures of from 0° C. to 100° C. are possible if the stability of the membranes and the solubility of the solution constituents permit. Generally, membrane life is longer at lower temperatures and power consumption will be lower at higher temperatures. Preferred operating temperatures are between 25° and 60° C., and more preferably, from 35° to 50° C. In the case of sulfuric acid, a temperature greater than 45° C. is most preferred.

The current passed through the water splitter is direct current of a voltage dictated by design and performance characteristics readily apparent to the skilled artisan and/or determined by routine experimentation. Current densities between 25 and 300 amps per square foot (between 28 and 330 milliamps per square centimeter) are preferred; and current densities between 50 and 150 amps per square foot (between 55 and 165 milliamps per square centimeter) are more preferred. Higher or lower current densities can be used for certain specific applications.

In electrodialysis and related processes, generally the flow rate through the stack is higher than the input rate of fresh feed. The stack is operated in a recycle mode with the recycle feed being obtained from a recycle reservoir. In this way, one can determine and adjust the net input rate to obtain the desired composition changes for the entire system even though the concentration change in one pass through the stack may be small. Feed to each recycle loop of the system and product removal may be made continuously (steady state operation) or periodically (batch operation).

The following examples illustrate the practice of the present invention and describe experimental methods to enable one skilled in the art to find the proper operating conditions to achieve product purity. The example should not be construed as limiting the invention to anything less than that which is disclosed or which would have been obvious to one of ordinary skill in the art therefrom. Percents and parts are by weight unless otherwise indicated.

EXAMPLE

The unexpected dependence of formic acid diffusion rate on base concentration is illustrated by Comparative Example 1, performed in a conventional three compartment water splitter, and Examples 1 and 2 in two compartment water splitters. In a three compartment water splitter of the type illustrated in FIG. 1, nor formic acid is expected to diffuse from the acid compartment (A) across the cation membrane 11c because of the intervening salt compartment (S). With such an arrangement, diffusion of formic acid to the base compartment (B) occurs only across the bipolar membrane 11b. Although diffusion of formic acid across the anion membrane may also occur, it is of no consequence to the purity of the base produced.

COMPARATIVE 1

Figure 5:
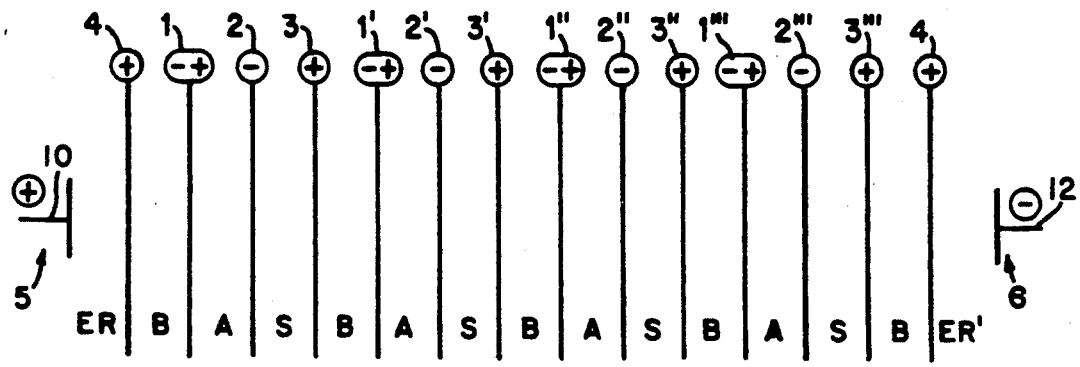
FIG. 5 is a schematic drawing of an electrodialytic stack used in the Comparative Example.

The water splitting was performed in a laboratory scale electrodialytic stack schematically illustrated in FIG. 5. The stack consisted of end plates 5 and 6 to which the electrodes were attached and through which solutions were fed to and removed from the stack. Gaskets used to separate the membranes and form the solution compartments (A, B and S) were 0.13 cm thick. Each gasket had an open central area of 23 cm² (through which current could pass) filled with a screen to keep the membranes separated and promote good flow distribution. Holes punched in the gaskets formed internal manifolds. Slots (ports) connecting the manifold with the open central area allowed parallel flow of solution in and out of each compartment. The stack consisted of a Ni anode 10, and electrode rinse compartment (ER), a DuPont Nafion ® 324 cation membrane 4, a base compartment (B), then 4 repeating cells consisting of bipolar membrane 1, acid compartment (A), anion membrane 2, salt compartment (S), cation membrane 3, and base compartment (B). The last base compartment (B) was followed by another Nafion ® 324 membrane 4, an electrode rinse compartment (ER') and a stainless steel cathode 12. The bipolar membranes were prepared according to U.S. Pat. No. 4,766,161. The cation membranes were prepared according to U.S. Pat. No. 4,738,764. The anion membranes were prepared from styrene vinylbenzyl chloride copolymer using the method as described for forming the anion layer of the bipolar membrane in Example 1 of U.S. Pat. No. 4,766,161.

Figure 6:
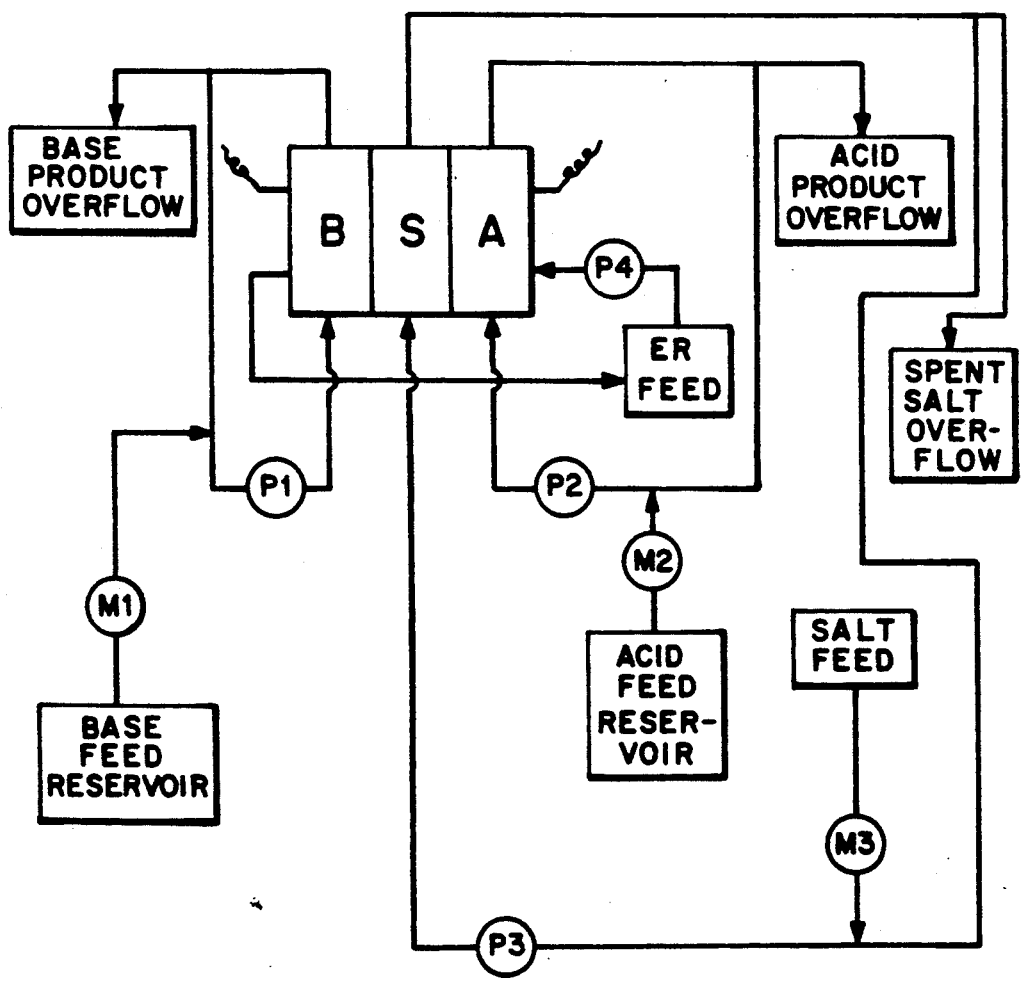
FIG. 6 is a schematic drawing of a diagram of the system used in the Comparative Example 1.

The stack was placed in the system shown schematically in FIG. 6 in order to carry out the water splitting process. Four pumps (P1-P4) were used to recirculate solution to the acid, base, salt and electrode rinse compartments at a rate of about 1 liter/minute. The metering pumps (M1, M2, M3) were set to a high flow, (ca. 100 mL/min) and the overflows from the recircuation loops (A), (B) and (S) were returned to their respective reservoirs so that a batch process was carried out. The acid and base reservoirs were calibrated so that the volume could be determined. Samples of acid and base were withdrawn periodically and analyzed. A mass balance for the system was thus available so that the current efficiencies for acid, base and formate transport to the base could be determined.

The system was charged as follows: Acid, 150 mL of a 5% sodium formate (NaFm) plus 8.5% formic acid (HFm) solution; Base, 200 mL of 2.5% NaOH; and Salt, 300 mL of 30% sodium formate. Pumping and a direct current of 2.5 A were started. During the experiment, the conductivity o salt remained about 0.13 S/cm, although its volume decreased due to water transport. The salt solution became basic (pH>10) soon after the current started and remained basic throughout the experiment. Thus, there was no formic acid in contact with the cation membrane. The concentrations of acid and base, as well as the base volume, as a function of time are shown in Table I. The sodium formate concentration in the base product was determined by ion chromatography. From the change in volume and composition for each time interval, the current efficiency was calculated.

TABLE I

Batch Production of NaOH and Formic Acid
3-Compartment Water Splitter

| Time (min) | Base [OH⁻] (m/L) | Base [NaFm] (m/L) | Acid [H⁺]* (m/L) | Base Sample Vol. (mL) | Base Vol. (mL) | Base Current Efficiency NaOH | Base Current Efficiency NaFm |
|---|---|---|---|---|---|---|---|
| 2 | 0.721 | 0.01 | 0.849 | 200 | 5.0 | — | — |
| 61 | 2.167 | 0.03 | 2.400 | 201 | 6.0 | 0.804 | 0.011 |
| 96 | 2.980 | 0.05 | 3.040 | 200 | 6.0 | 0.797 | 0.019 |
| 135 | 3.690 | 0.08 | 3.660 | 200 | 6.0 | 0.659 | 0.026 |
| 186 | 4.500 | 0.12 | 4.250 | 203 | 7.0 | 0.623 | 0.028 |
| 223 | 5.010 | 0.15 | 4.560 | 205 | 5.0 | 0.631 | 0.031 |

*Acid concentration was determined 1 minute after the base.

Figure 7:
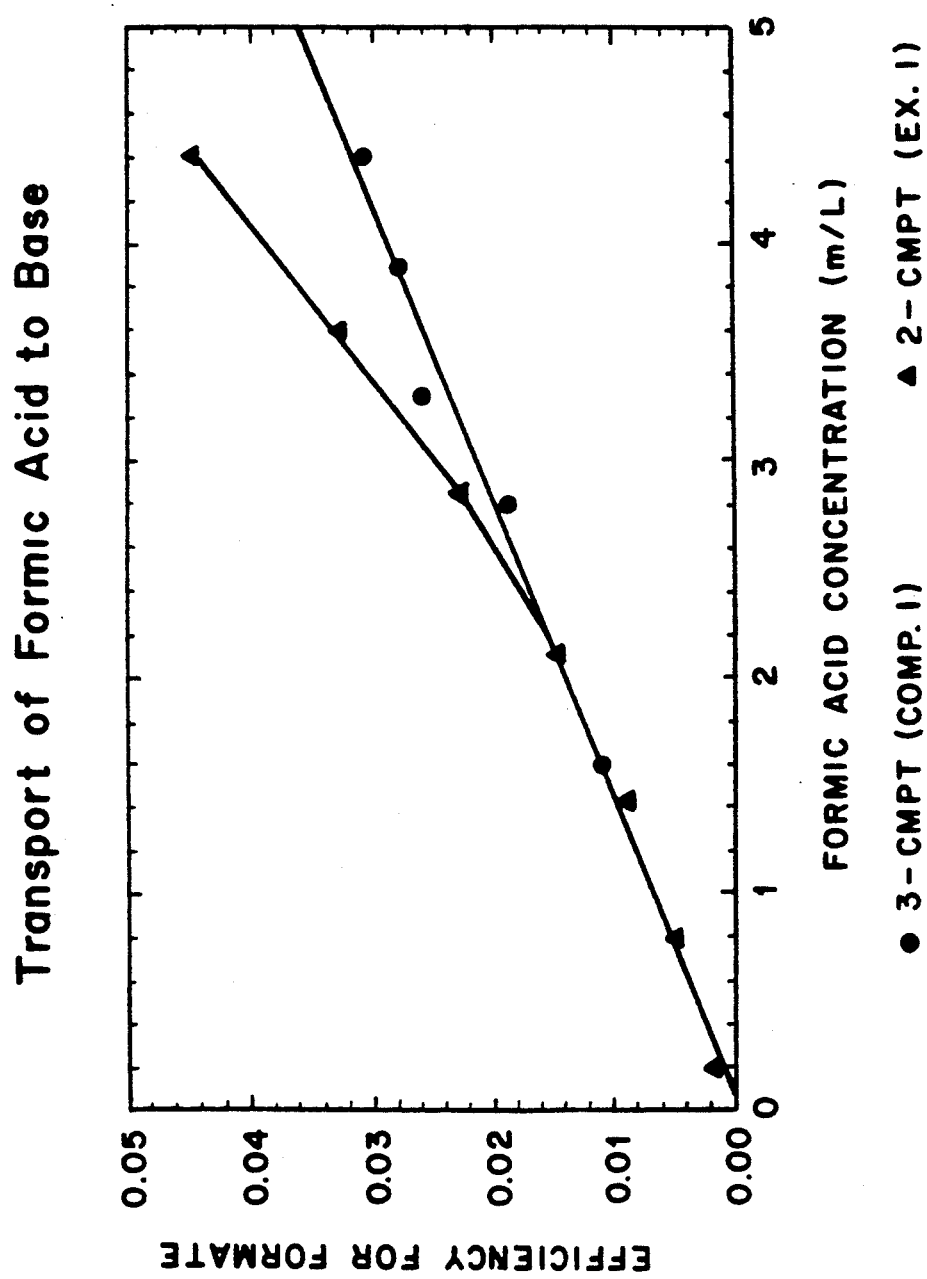
FIG. 7 is a graph of the current efficiency of formate formation in the base compartment (B) as a function of acid concentration in the acid compartment (A) for Comparative Examples 1 and 2.

When the transport rate of sodium formate across the bipolar membrane from the acid compartment (A) to the base compartment (B), reported as the NaFm current efficiency, is plotted against the formic acid concentration, a straight line results. This is the expected result of Fickian diffusion. (FIG. 7).

COMPARATIVE 2

The same stack as used in Comparative Example 1 was used except that the anion membranes 2, 2', 2" and 2'" and salt compartments (S) were removed. The base feed reservoir was filled with water which was fed to the recirculation loop at a slow rate so a feed and bleed operation resulted. The overflow from the base loop was collected for analysis. The base recirculation loop was charged with 100 mL of about 2.5N NaOH. The acid reservoir, being run in batch mode, was charged with about 750 g of 35% sodium formate. The experiment was started at a current of 2.5 A. For about the first 2 hours, 35% NaOH was added to the acid, neutralizing the formic acid as it was formed, to maintain pH 7. When the concentration of NaOH overflowing from the base was essentially constant, base sample collection over 15 minute intervals was begun and the addition of NaOH to the acid was stopped. Samples of acid were titrated periodically to determine the formic acid concentration. In addition to the base concentration, the concentration of sodium formate in some of the base samples was determined by ion chromatography. Since the acid concentration was increasing rapidly during the experiment, the concentration of sodium formate in the base was not near steady state. The ultimate steady state concentration was estimated by the formula:

$$C = C_f - (C_f - C_0) \exp(-kt/V)$$

In this formula C is the concentration at time t, V is the volume of the system, $C_f$ is the steady state concentration $C_0$ is the concentration at 0 time and k is the overflow rate. In order to facilitate calculation, a second order least squares regression was used to fit the NaOH and sodium formate concentrations and base overflow rate versus time. The values calculated in this way were within the error range of the experimental values as shown in Table II. The calculated efficiency for NaOH and sodium formate production in the base compartment (B) are shown in Table III along with the formic acid concentration. The efficiency for formate formation in the base compartment (B) as a function of acid concentration in the acid compartment (A) is plotted in FIG. 7 along with the result from Comparative Example 1. The unexpected non-linear dependence of rate on concentration difference for this Example is shown clearly. The result non-linearity is caused by diffusion of formic acid across the cation membrane to the base compartment (B) and shows an unexpected concentration dependence. The initially linear portion of the curve probably reflects the diffusion of formic acid mainly across the bipolar membrane since the rate is about the same as in Comparative Example 1. When the formic acid concentration in the acid compartment (A) exceeded a critical value (about 2.5 m/L) which generally is dependent on the base concentration and the cation exchange membrane properties, formic acid diffusion across the cation membrane increased rapidly.

Diffusion of formic acid to the base compartment (B) was substantial in the prior art method. During the last interval the mole ratio of NaOH/NaFm collected in the base compartment (B) was 18.

Example 2 below shows how this diffusion and the resulting contamination can be reduced by proper control of the base concentration.

TABLE II

Observed and Calculated Concentration and Overflow Rates in 2-Compartment Water Splitter

| Time (Min) | NaOH Normality obs. | NaOH Normality calc. | Overflow (g/min) obs. | Overflow (g/min) calc. | Normality NaFm obs. | Normality NaFm calc. |
|---|---|---|---|---|---|---|
| 0 | 2.850 | 2.847 | 1.819 | 1.829 | 0.016 | 0.019 |
| 15 | 2.856 | 2.845 | 1.834 | 1.833 | | |
| 30 | 2.840 | 2.841 | 1.843 | 1.839 | 0.019 | 0.016 |
| 45 | 2.824 | 2.837 | 1.858 | 1.846 | | |
| 60 | 2.822 | 2.831 | 1.861 | 1.855 | 0.022 | 0.020 |
| 75 | 2.822 | 2.824 | 1.857 | 1.864 | | |
| 90 | 2.806 | 2.816 | 1.877 | 1.875 | 0.032 | 0.030 |
| 105 | 2.806 | 2.807 | 1.912 | 1.888 | | |
| 120 | 2.806 | 2.796 | 1.867 | 1.901 | 0.044 | 0.046 |
| 135 | 2.798 | 2.786 | 1.917 | 1.916 | | |
| 150 | 2.784 | 1.772 | 1.923 | 1.933 | 0.063 | 0.069 |
| 165 | 2.764 | 2.758 | 1.951 | 1.950 | | |
| 180 | 2.722 | 2.743 | 1.981 | 1.969 | 0.101 | 0.097 |

TABLE III

Calculated Efficiency and Acid Concentration
In 2-Compartment Water Splitter

| Time (min) | Base D. (g/mL) | HFm (m/L) | Current Efficiency NaFm | Current Efficiency NaOH |
|---|---|---|---|---|
| 0 | 1.106 | 0.20 | 0.002 | 0.757 |
| 30 | 1.106 | 0.80 | 0.005 | 0.760 |
| 60 | 1.106 | 1.43 | 0.009 | 0.763 |
| 90 | 1.102 | 2.12 | 0.015 | 0.771 |
| 120 | 1.106 | 2.84 | 0.023 | 0.773 |
| 150 | 1.108 | 3.60 | 0.033 | 0.778 |
| 180 | 1.108 | 4.41 | 0.045 | 0.784 |

EXAMPLE 1

Figure 8:
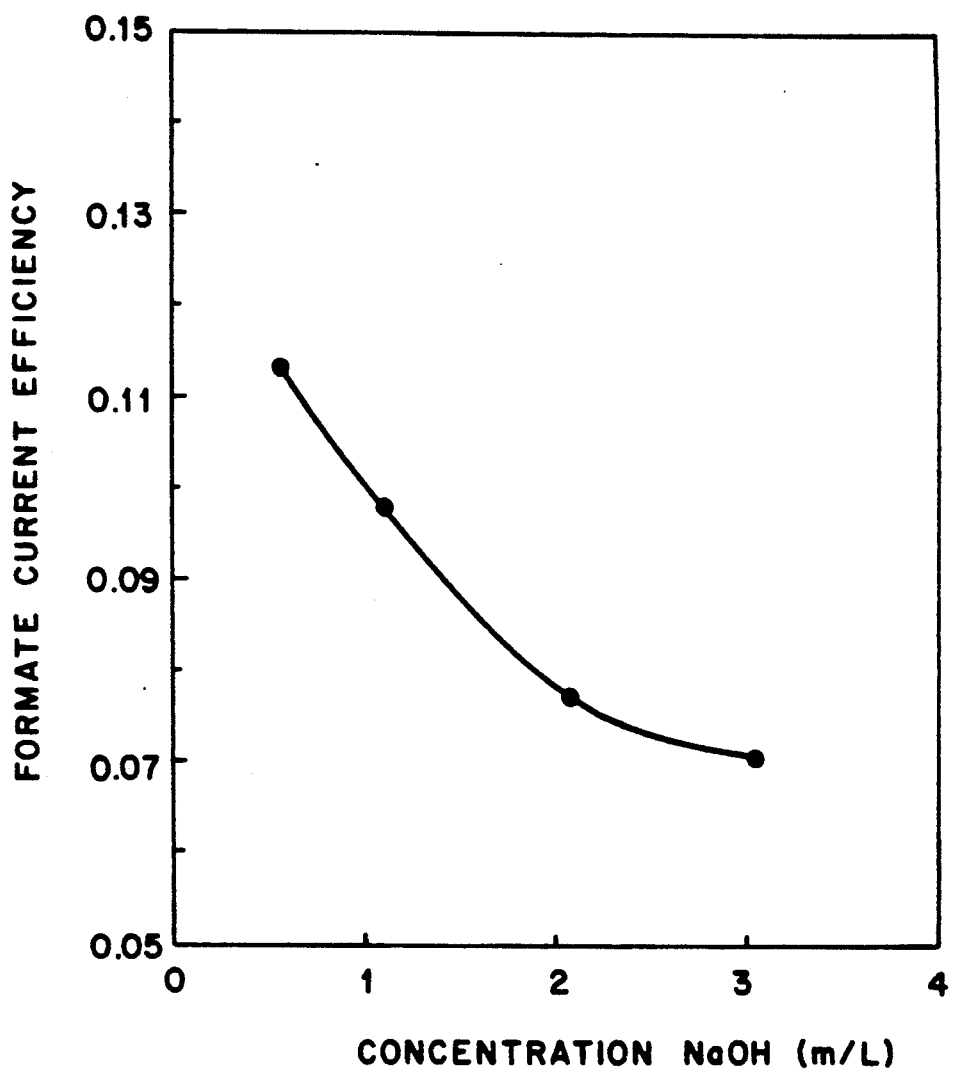
FIG. 8 is a graph of the current efficiency of formate as a function of NaOH concentration in the base compartment (B).

The same apparatus and method as for Comparative 2 were used to determine the effect of base concentration on product purity with the results shown in Table IV. The membranes in the stack were not identical but were of the same type as in Comparative Example 2. The repeating unit cell has the same configuration as shown in FIG. 2. A current of 2.0 A instead of 2.5 A was used. Because the duration of each run was relatively short (about 0.5 hour), the system was not at steady state. The rate of change of concentration and product flux were used to estimate the current efficiency. In between each run, the make-up rate to the base was increased. The efficiency (fraction of current resulting in product) for NaOH and sodium formate is shown in Table IV. For runs A-D at successively lower base concentrations, the mole ratio of NaOH to sodium formate produced was 10.3, 9.8, 8.3, 7.3. This clearly shows the importance of operating at high NaOH concentration in order to improve the purity of the base product. The formate current efficiency (transport rate) is plotted in FIG. 8. The lower rate a higher base concentration is evident.

TABLE IV

| Run | Acid concentration (% Formic Acid) Initial | Final | Base Concentration (moles/L NaOH) Initial | Final | Na Formate in (mols g/L) Initial | Final | Base NaOH | Current Efficiency NaFm |
|---|---|---|---|---|---|---|---|---|
| A | 17.3 | 19.0 | 3.12 | 2.99 | 0.160 | 0.160 | 0.719 | 0.070 |
| B | 18.1 | 20.2 | 2.14 | 2.02 | 0.189 | 0.193 | 0.753 | 0.077 |
| C | 17.7 | 19.3 | 1.16 | 1.01 | 0.115 | 0.115 | 0.815 | 0.098 |
| D | 17.4 | 18.4 | 0.60 | 0.52 | 0.070 | 0.069 | 0.821 | 0.113 |

EXAMPLE 2

The same type of two compartment water splitter as used for Comparative 2 was operated using a feed and bleed arrangement for both the acid and base. The acid loop was charged with 15% HFm and 5% NaFm and the base loop with 10% NaOH (without NaFm). The Acid Feed reservoir was supplied with 300 g/L (NaFm) and the Base Feed reservoir with water. The experiment was run and samples analyzed as for Example 1 with the results shown in Table V.

TABLE V

| TIME INTERVAL (MIN) | ACID PRODUCT PRDT. RATE (g/min) | CONC. HFm (meq/g) | BASE PRODUCT PRDT. RATE (g/min) | CONC. NaOH (meq/g) | NaFm (meq/g) |
|---|---|---|---|---|---|
| 17–40 | 1.73 | 1.64(12.0%) | 1.42 | 2.21 | 0.070 |
| 87–105 | 2.80 | 2.32(10.7%) | 1.49 | 2.42 | 0.125 |
| 170–191 | 1.85 | 2.17(10.0%) | 1.51 | 2.53 | 0.139 |
| 147–271 | 1.85 | 2.13(9.8%) | 1.49 | 2.57 | 0.140 |

The temperature (38° C.) and the stack potential (11.2) volts were stable after the first 100 minutes. Based on the production rate of acid, the calculated current efficiency was 0.79, and based on base the calculated efficiency was 0.77. The mole ratio of NaOH/NaFm in the base collected during the last interval was 18, (current efficiency for formate transport of 0.04). Considering the lower formic acid concentration in this Example, the formate transport of this Example is comparable to formate transport in Example 1, at the higher base concentrations of Example 1. Thus, the base concentration was high enough to prevent acid transport across the cation membrane.

EXAMPLE 3

Figure 9:
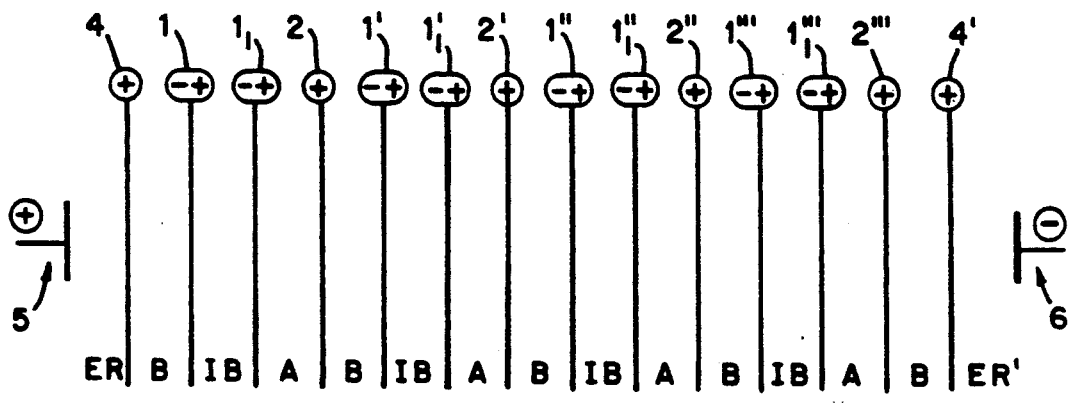
FIG. 9 is a schematic drawing of a stack used in Example 3.
Figure 10:
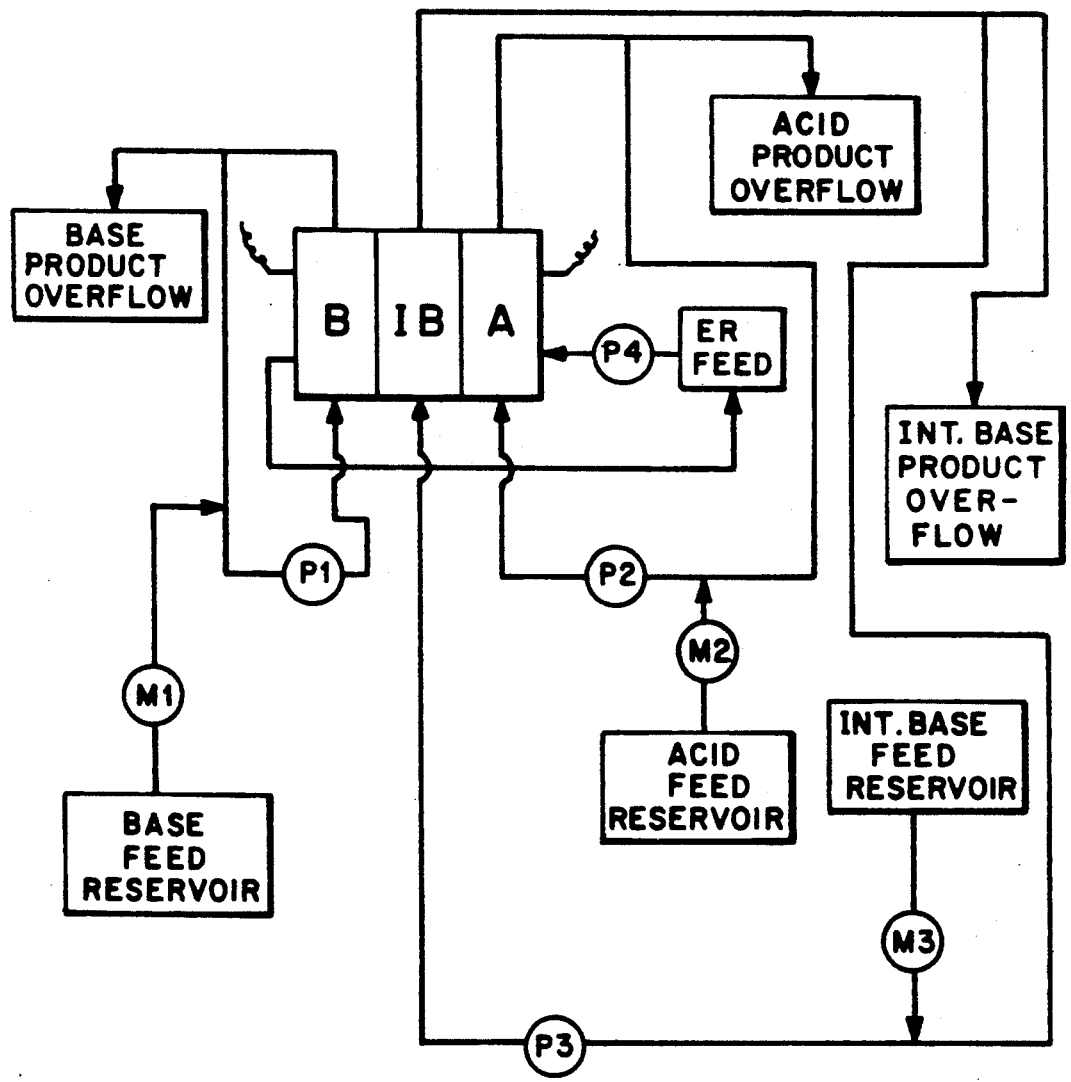
FIG. 10 is a schematic drawing of a system used in Example 3.

A laboratory scale electrodialysis stack was assembled as shown schematically in FIG. 9 and used in the system shown in FIG. 10. Common elements in FIGS. 5 and 9 and in FIGS. 6 and 10 have the same reference characters. There was a nickel anode 5 and stainless steel cathode 6, eight bipolar membranes $(-+)$ 1, $1_1$, 1', $1_1'$, 1", $1_1''$, 1''', and $1_1'''$, prepared according to U.S. Pat. No. 4,766,161, four cation membranes $(+)$ 2, 2', 2" and 2''' prepared according to U.S. Pat. No. 4,738,764 and two fluorinated cation membranes $(+)$ 4, and 4' Nafion ® 324 (DuPont) which were placed closest to the electrodes. The membranes were separated from one another by 0.13 cm thick gaskets which were punched to form three sets of internal manifolds and three sets of solution compartments labeled B, IB, and A in FIG. 310. The electrode rinse compartments, ER and ER' between the electrodes and Nafion ® membranes were externally manifolded. The exposed area of each membrane in the cell was about 23 $cm^2$. A stack of four unit cells was thus formed.

The stack was placed in the system shown schematically in FIG. 10 in order to carry out the water splitting process. Four pumps (P1-P4) were used to recirculate solution to the A, B, IB and ER compartments at a rate of about 1 L/min. The recirculation loops for the A, B, and IB compartments were fed at constant rates from feed reservoirs labeled Base Feed, Acid Fee and Int. (Intermediate) Base Feed in the diagram using metering pumps M1-M3. The addition of solution to the recirculation loops caused an overflow of solution at the points labeled Base Product, Acid Product and Int. (Intermediate) Base Product.

To begin the experiment, the recirculation loops, each with a volume of about 100 mL, were charged with solution as follows: B—15% NaOH+1% sodium formate (NaFm); A—5% NaFm+15% formic acid (HFm); IB—2.2% NaOH+1% NaFm. Solution was placed in the feed reservoirs as follows: Base Feed—water; Acid Feed—300 g/L NaFm; Int. Base Feed—1N NaOH+0.70 g/L NaFm, ER Feed 1N NaOH. A direct current of 2.0 Amps, feeds at about 1.5 mL/min to B, 1.0 mL/min to IB and 1.8 mL/min to A, and a timer were started to begin the experiment. Samples of the overflowed Acid, Base, and Int. Base Products were collected over timed intervals and analyzed for formic acid or NaOH by titration to pH 8.5 with standard acid and base and formate ion by ion chromatography. The results are shown in Table VI.

TABLE VI

| TIME INTERVAL (MIN) | ACID PRODUCT PRDT. RATE (g/min) | CONC. HFm (meq/g) | BASE PRODUCT PRDT. RATE (g/min) | NaOH (meq/g) | CONC. NaFm (meq/g) | INT. BASE PRODUCT PRDT. RATE (g/min) | NaOH (meq/g) | CONC. NaFm (meq/g) |
|---|---|---|---|---|---|---|---|---|
| 47–10 | 1.84 | 2.35 | 1.59 | 2.80 | 0.072 | 1.02 | 0.68 | 0.138 |
| 122–145 | 1.88 | 2.13 | 1.55 | 2.59 | 0.038 | 1.03 | 0.87 | 0.144 |
| 184–107 | 1.93 | 2.10 | 1.55 | 2.56 | 0.026 | 0.97 | 0.93 | 0.145 |
| 281–307 | 1.79 | 2.09 | 1.52 | 2.56 | 0.019 | 0.95 | 0.05 | 0.141 |

The efficiency for formate transport was only 0.006 in indicating that the improved cell configuration was able to reduce formate transport across the bipolar membrane into the base compartment (B) and that the high base concentration was able to greatly reduce formate transport across the cation membrane.

While exemplary embodiments of the invention have been described, the true scope of the invention is to be determined from the following claims.

What is claimed is:

1. A method for reducing diffusion of neutral weak acid across cation membranes of an electrodialysis apparatus which from a salt of a weak acid, produces a base having an increased base to salt concentration ratio which is greater than the base to salt concentration ratio of a base product not so produced, the apparatus comprising at least one cell comprising at least one water splitter means to convert water to $H^+$ and OH and a cation selective membrane adjacent to the water splitter means, there being a base compartment (B) between the cation selective membrane and water splitter means located to receive OH from the water splitter means and a salt feed compartment adjacent to the cation membrane opposite the base compartment (B), the cation selective membrane having an outer surface facing away from the base compartment (B), comprising the steps of:

contacting the outer surface of the cation membrane with a solution of a salt of a weak acid, feeding an aqueous stream to the base compartment (B), applying a sufficient electrical potential across the cell to cause introduction of OH from the means for splitting water into the base compartment (B), and transport of cations from the salt solution across the cation membrane into the solution (B) to form base, the anions remaining in the salt compartment (S) forming acid with $H^+$ passing into the salt compartment (S);

monitoring the concentration in the base compartment (B) of base formed and weak acid which leaks into the base compartment (B);

maintaining the base concentration in the base compartment (B) at a concentration sufficient to reduce the diffusion of said weak acid across said cation membrane thereby increasing said concentration ratio of base to salt in the base compartment (B).

2. The method as recited in claim 1 wherein the acid has an ionization constant of less than about $10^{-3}$.

3. The method as recited in claim 1 wherein the acid is a carboxylic acid.

4. The method as recited in claim 1 wherein the salt is selected from the group consisting of alkali metal formates, alkali metal acetates.

5. The method as recited in claim 4 wherein the salt is sodium formate.

6. The method of claim 1 wherein the apparatus comprises:

at least one unit cell comprising:

at least two serially aligned adjacent means for splitting water, there being an intermediate compartment between adjacent means; and at least one cation selective means adjacent to at least one of the means for splitting water, there being a product compartment between said cation selective means and the means for splitting water, and a feed compartment adjacent to the cation selective means opposite the product compartment, the aqueous salt solutions being fed to the feed compartments; and further comprising the steps of:

feeding an aqueous stream optionally comprising a base to the intermediate compartment;

removing the base from the product compartment; and removing the resultant intermediate product from the intermediate compartment.

7. A method for reducing diffusion of neutral weak base across anion membranes of an electrodialytic apparatus which from a salt of a weak base produces an acid having an acid to salt concentration ratio which is greater than the acid to salt concentration ratio of an acid product not so produced, the apparatus comprising at least one water splitter means to convert water to $H^+$ and OH and a anion selective membrane adjacent the water splitter means located to receive $H^+$ from the water splitter means and a salt feed compartment adjacent to the anion membrane opposite the acid compartment (A), the anion selective membrane having an outer surface facing away from the acid compartment (A) located to receive OH from the water splitter means, comprising the steps of:

contacting the outer surface of the anion membrane with a solution of a salt of a weak base, feeding an aqueous stream to the acid compartment (A), applying a sufficient electrical potential across the cell to a cause introduction of $H+$ from the means for splitting water into the acid compartment (A), and transport of anious from the salt solution across the anion membrane into the acid compartment (A) to form acid, the cations remaining in the salt compartment (A) forming base with OH— passing into the salt compartment (A);

monitoring the concentration in the acid compartment (A) of acid formed and weak base which leaks into the acid compartment (A);

maintaining the acid concentration in the acid compartment (A) at a concentration sufficient to reduce diffusion of weak acid across said anion membrane thereby increasing said concentration ratio of acid to salt in the acid compartment (A).

8. The method as recited in claim 7 wherein the base has an ionization constant of less than about $10^{-3}$.

9. The method as recited in claim 8 wherein the base is a ammonium.

10. The method of claim 7 wherein the apparatus comprises a method for generating acid having improved purity from an aqueous salt solution, comprising the steps of:

at least two serially aligned adjacent means for splitting water, there being an intermediate compartment between adjacent means; and at least one anion selective means adjacent to at least one of the means for splitting water, there being a product compartment between said anion selective means and the means for splitting water, and a feed compartment adjacent to the anion selective means opposite the product compartment, the aqueous salt solutions being fed to the feed compartments; and further comprising the steps of:

feeding an aqueous stream optionally comprising an acid to the intermediate compartment;

removing the acid from the product compartment; and removing the intermediate product from the intermediate compartment.

* * * * *

UNITED STATES PATENT AND TRADEMARK OFFICE
CERTIFICATE OF CORRECTION

PATENT NO. : 5,198,086
DATED : March 30, 1993
INVENTOR(S) : F.P. Chlanda et al.

It is certified that error appears in the above-identified patent and that said Letters Patent is hereby corrected as shown below:

Col. 19, Line 14 "OH" should read -- OH- --.
Col. 19, Line 18 "OH" should read -- OH- --.
Col. 19, Line 19 "OH" should read -- OH- --.
Col. 20, Line 14 "OH" should read -- OH- --.
Col. 20, Line 21 "OH" should read -- OH- --.

Signed and Sealed this

Eighth Day of February, 1994

BRUCE LEHMAN

*Attest:*

*Attesting Officer*   *Commissioner of Patents and Trademarks*